United States Patent
Schmidt et al.

(10) Patent No.: US 8,983,574 B2
(45) Date of Patent: Mar. 17, 2015

(54) CATHETER DEVICE WITH LOCAL MAGNETIC RESONANCE IMAGING COIL AND METHODS FOR USE THEREOF

(75) Inventors: Ehud Schmidt, Newton, MA (US); Rafael Diana, Sutton, MA (US)

(73) Assignee: The Brigham and Women's Hospital, Boston, MA (US)

( * ) Notice: Subject to any disclaimer, the term of this patent is extended or adjusted under 35 U.S.C. 154(b) by 87 days.

(21) Appl. No.: 13/509,719

(22) PCT Filed: Nov. 17, 2010

(86) PCT No.: PCT/US2010/057000
§ 371 (c)(1),
(2), (4) Date: Aug. 28, 2012

(87) PCT Pub. No.: WO2011/062971
PCT Pub. Date: May 26, 2011

(65) Prior Publication Data
US 2012/0316429 A1    Dec. 13, 2012

Related U.S. Application Data

(60) Provisional application No. 61/261,842, filed on Nov. 17, 2009.

(51) Int. Cl.
| A61B 5/05 | (2006.01) |
| G01R 33/34 | (2006.01) |
| G01R 33/28 | (2006.01) |
| A61B 5/027 | (2006.01) |
| A61B 5/055 | (2006.01) |

(52) U.S. Cl.
CPC .......... *G01R 33/34084* (2013.01); *G01R 33/28* (2013.01); *A61B 5/055* (2013.01); *G01R 33/286* (2013.01)

USPC .................................. 600/423; 600/585

(58) Field of Classification Search
USPC ................................................ 600/423
See application file for complete search history.

(56) References Cited

U.S. PATENT DOCUMENTS

| 5,307,814 A | 5/1994 | Kressel et al. |
| 5,451,232 A | 9/1995 | Rhinehart et al. |
| 5,733,294 A * | 3/1998 | Forber et al. ............... 606/151 |

(Continued)

OTHER PUBLICATIONS

International Search Report and Written Opinion as mailed on Jun. 24, 2011 for International Application No. PCT/US2010/057000.

*Primary Examiner* — Long V Le
*Assistant Examiner* — Kevin Pontius
(74) *Attorney, Agent, or Firm* — Quarles & Brady, LLP

(57) ABSTRACT

A catheter device for deploying a local magnetic resonance imaging (MRI) coil is provided. The catheter device includes an outer catheter shaft having a lumen extending from a proximal end to a distal end and an inner catheter shaft having a lumen extending from a proximal end to a distal end. The outer and inner catheter shafts are movably engaged such that one can move relative to the other. A plurality of non-metallic filaments are coupled on one end to the outer catheter shaft and coupled on another end to the inner catheter shaft. The plurality of non-metallic filaments are intertwined to form a braid, to which a local MRI coil is coupled. The local MRI coil is configured to have a circular shape when the braid is in a deployed position. Additionally, motion tracking coils can be coupled to the braid to provide motion tracking information for motion compensation.

22 Claims, 6 Drawing Sheets

(56) References Cited

U.S. PATENT DOCUMENTS

| | | | |
|---|---|---|---|
| 6,171,240 B1 | 1/2001 | Young et al. | |
| 6,216,044 B1 | 4/2001 | Kordis | |
| 6,263,229 B1 | 7/2001 | Atalar et al. | |
| 6,280,385 B1 | 8/2001 | Melzer et al. | |
| 6,437,569 B1 | 8/2002 | Minkoff et al. | |
| 6,628,980 B2 | 9/2003 | Atalar et al. | |
| 6,950,063 B2 | 9/2005 | Nesteruk et al. | |
| 7,172,624 B2 | 2/2007 | Weber et al. | |
| 7,551,953 B2 | 6/2009 | Lardo et al. | |
| 7,722,604 B2 | 5/2010 | Brown, III et al. | |
| 7,725,160 B2 * | 5/2010 | Weber | 600/423 |
| 7,766,958 B2 | 8/2010 | Alt et al. | |
| 7,848,788 B2 | 12/2010 | Tulley et al. | |
| 7,912,531 B1 * | 3/2011 | Chiu et al. | 600/423 |
| 8,412,306 B2 * | 4/2013 | Kurpad et al. | 600/423 |
| 2002/0045816 A1 | 4/2002 | Atalar et al. | |
| 2005/0215886 A1 * | 9/2005 | Schmidt | 600/423 |
| 2006/0178576 A1 | 8/2006 | Weber et al. | |
| 2007/0106148 A1 * | 5/2007 | Dumoulin | 600/410 |
| 2007/0238979 A1 * | 10/2007 | Huynh et al. | 600/420 |
| 2008/0262337 A1 | 10/2008 | Falwell et al. | |
| 2009/0171187 A1 * | 7/2009 | Gerhart et al. | 600/421 |
| 2009/0192601 A1 | 7/2009 | Rafiee et al. | |

\* cited by examiner

CATHETER DEVICE WITH LOCAL MAGNETIC RESONANCE IMAGING COIL AND METHODS FOR USE THEREOF

CROSS-REFERENCE TO RELATED APPLICATIONS

This application represents the U.S. National Stage of International Application No. PCT/US2010/057000, filed Nov. 17, 2010 which claims the benefit of U.S. Provisional Patent Application Ser. No. 61/261,842, filed on Nov. 17, 2009, and entitled "Catheter Device, Catheter System, and Method of Using the Same." The foregoing applications are incorporated herein by reference in their-entirety.

BACKGROUND OF THE INVENTION

The field of the invention is medical devices and methods for their use. More particularly, the invention relates to a catheter device for ablation or other medical procedures that is configured for magnetic resonance imaging.

Magnetic resonance imaging ("MRI") is considered to be the leading medical imaging modality for monitoring ablation therapies, such as thermal radio frequency ablation in the heart. MRI is capable of utilizing a variety of pulse sequences to monitor the treated tissues for scar formation, temperature elevation, creation of edema, changes in tissue stiffness, changes in elasticity, and the like. MRI is limited, however, in that the use of a surface coil external to the patient's body is required. Such external surface coils restrict imaging to longer scan times that can take several minutes. Alternatively, shorter scan times on the order of a few seconds can be used, but these scan times result in the production of images having very low, and therefore clinically insufficient, spatial resolution. The reason for these limitations is that MRI surface coils have relatively low signal-to-noise ("SNR") ratios.

One solution to this problem is to use local coils, which can be placed close to the area of interest. While these coils have a smaller field-of-view, they can possess SNRs which are five to ten times that of surface coils. Thus, imaging with a local coil, to obtain the equivalent spatial resolution from an external surface coil, may be conducted at a much faster pace than with surface coils. One example of such a coil is an endorectal coil, which is used for high-resolution prostate imaging. These local coils, while beneficial for the reasons stated above, are more prone to motion artifacts because when the imaged anatomy is moving, these coils will move with the anatomy, thereby resulting in blurred images.

In the context of vascular imaging, there are additional demands on local coils. First, they must be small enough to be inserted via small access vessels to the desired area of operation. Second, they must be designed so as not to block vessels during introduction or during use. Third, for use in therapy, it is preferred that local coils be introduced together with the ablation devices, or other common interventional devices, and that they do not interfere with the ablation process. Fourth, it would be preferable if they can be rapidly moved from site to site during the therapeutic process.

It would therefore be desirable to provide a catheter device that provides both an ablation, or other medical, device to a target region in addition to a clinically useful local coil for MRI. Such a catheter device would desirably not interfere with blood flow during its delivery or operation. It would be additionally desirable if such a catheter device had a reduced susceptibility to motion and the resulting artifacts therefrom in reconstructed images.

SUMMARY OF THE INVENTION

The present invention overcomes the aforementioned drawbacks by providing a catheter device having a braid formed of non-metallic filaments, to which a local magnetic resonance imaging ("MRI") coil is coupled. In particular, the braid is designed to expand and retract so as to provide a reduced profile during initial positioning of the catheter device and be deployed to an expanded configuration designed to configure the local MRI coil coupled thereto for imaging.

It is an aspect of the invention to provide a catheter device for deploying a local MRI coil. The catheter device includes an outer catheter shaft having a lumen extending from a proximal end to a distal end and an inner catheter shaft having a lumen extending from a proximal end to a distal end. The outer and inner catheter shafts are movably engaged such that one can move relative to the other. A plurality of non-metallic filaments are coupled on one end to the outer catheter shaft and coupled on another end to the inner catheter shaft. The plurality of non-metallic filaments are intertwined to form a braid, to which a local MRI coil is coupled. The local MRI coil is configured to have a circular shape when the braid is in a deployed position. Additionally, motion tracking coils can be coupled to the braid to provide motion tracking information for motion compensation.

It is another aspect of the invention to provide a local MRI coil system. The local MRI coil system includes a catheter extending from a proximal end to a distal end to form a lumen extending therebetween, and a shaft having a lumen extending from a proximal end to a distal end. The shaft is movably engaged with the catheter to move between a first position proximate to the proximal end of the catheter and a second position proximate to the distal end of the catheter. A plurality of non-metallic filaments are coupled to extend between the catheter and the shaft to form a braid configured to move between a retracted position and a deployed position as the shaft is moved between the first and second positions. A local MRI coil loop is coupled to the braid and configured to compress with the braid in the retracted position and expand into a substantially circular shape with the braid in the deployed position.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

By way of overview and introduction, a catheter device 100 that can provide imaging and motion tracking coils for magnetic resonance imaging ("MRI") is generally illustrated in FIGS. 1-7. As will be described, one advantageous clinical use of the catheter device 100 is intra-cardiac medical procedures, such as ablation procedures and the like. The catheter device 100 can be used to monitor a therapy, such as a radio frequency ablation ("RFA") therapy for cardiac atrial fibrillation, using MRI to acquire images during the therapy so that the therapy can be monitored and adjusted as needed. It is noted that the portion of the radio frequency range employed by RFA is significantly lower than the portion of the radio frequency range employed for MRI. For example, RFA probes commonly operate at frequencies around 500 kilohertz, whereas MRI systems commonly operate at frequencies higher than 20 megahertz. The catheter device 100 can also be used for other vascular and non-vascular treatment applications when MRI imaging can be of benefit, such as the placement of stents and angioplasty balloons.

Figure 1:
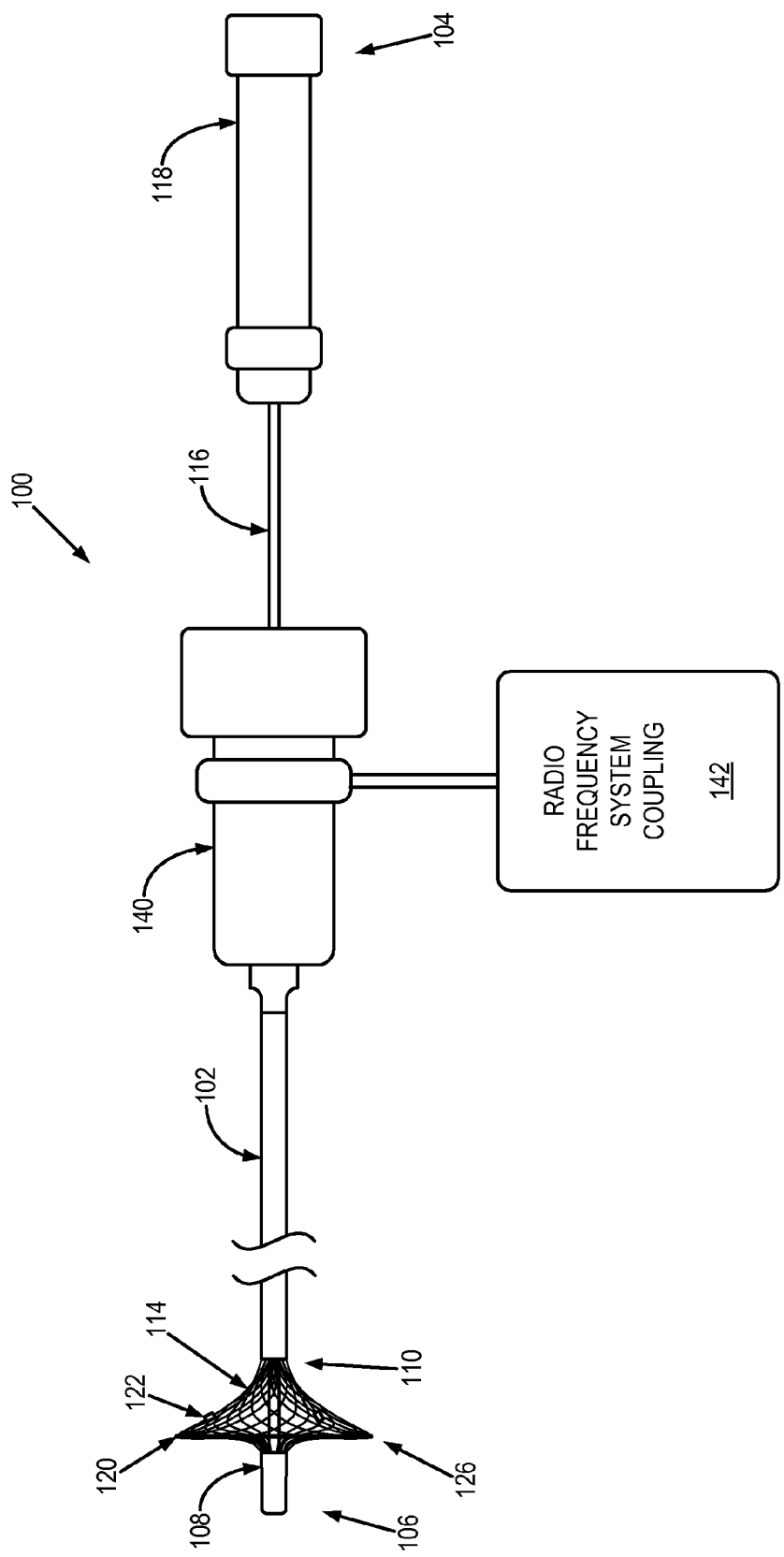
FIG. 1 is a diagram of an exemplary catheter device including a local magnetic resonance imaging ("MRI") coil.

Referring to FIG. 1, the catheter device 100 includes an outer catheter shaft 102 having a lumen (not shown in FIG. 1) extending from a proximal end 104 of the catheter device 100 to a distal end 106 of the catheter device 100. A tip 108 may be positioned distal to a distal end 110 of the catheter shaft 102. As will be detailed, the tip 108 has a lumen that is dimensioned similar to the lumen of the outer catheter shaft 102. An inner catheter shaft 116 is movably, such as slidably, engaged with the outer catheter shaft 102, and has a lumen 112 (FIG. 3) extending from the proximal end 104 of the catheter device 100 to the distal end 106 of the catheter device 100. A braid 114 is formed by a plurality of non-metallic filaments coupled to and extending from the distal end 110 of the outer catheter shaft 102 towards the distal end of the inner catheter shaft 116. In some configurations, the non-metallic filaments are coupled to the tip 108, which is in turn coupled to the inner catheter shaft 116. The braid 114 is configured to move between a retracted position (FIG. 6) and a deployed position (FIG. 2), as will be described in detail below.

The inner catheter shaft 116 may be coupled at its proximal end to a handle 118 that, when manipulated, causes the inner catheter shaft 116 to move relative to the outer catheter shaft 102. As mentioned above, the inner catheter shaft 116 may be coupled at its distal end to the tip 108 so that actuation of the inner catheter shaft 116 causes the tip 108 to move in relation to the distal end 110 of the outer catheter shaft 102, thereby shortening a distance between the distal end 110 of the outer catheter shaft 102 and the distal end of the inner catheter shaft 116. As will be described in further detail below, the shortening of this distance compresses the filaments that form the braid 114, which forces the braid 114 to radially expand into its deployed position. In alternative configurations, the outer catheter shaft 102 may be coupled to the handle 118, such that manipulation of the handle 118 causes the outer catheter shaft 102 to move in relation to the inner catheter shaft 116. In such cases and other contemplated configurations, the outer catheter shaft 102 may move along the inner catheter shaft 116 to shorten the distance between the distal end 110 of the outer catheter shaft 102 and the distal end of the inner catheter shaft 116 and compresses the filaments that form the braid 114 its deployed position. The lumen 112 of the inner catheter shaft 116 may be sized to receive a medical device 124 (FIG. 4), such as an RFA catheter; other electrophysiology ablation catheters, including laser ablation and cryoablation catheters; a stenting catheter; or a balloon angioplasty catheter. The lumen 112 can also be used to extrude liquid at fixed rates in order to cool the RFA catheter during heating, or to displace tissues, such as cardiac wall tissue, for measurements of elastic constants of the tissues.

Figure 2:
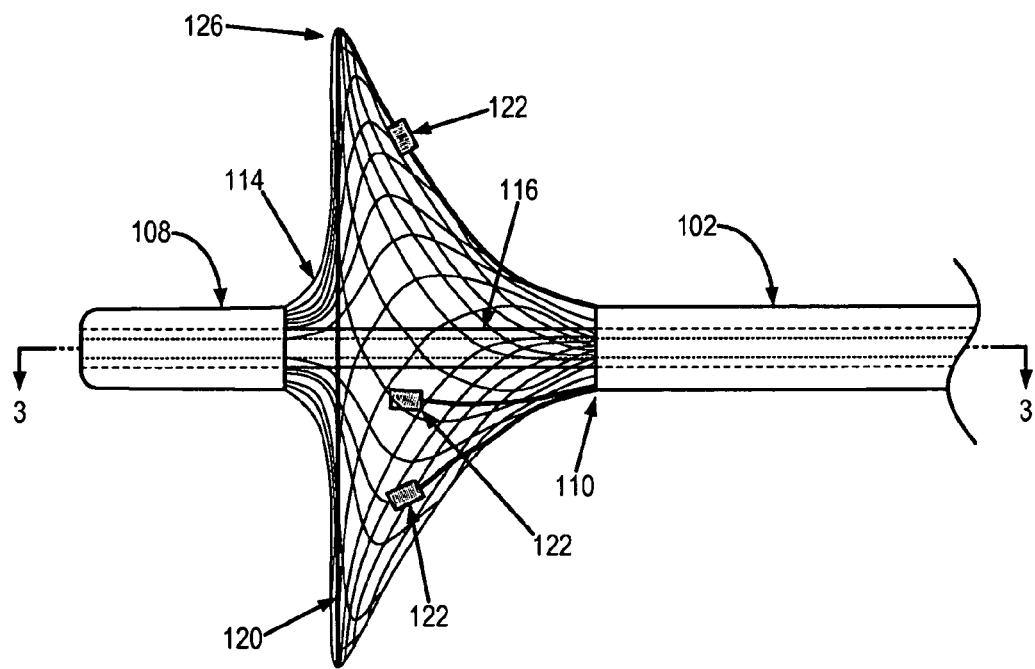
FIG. 2 is an elevation view of an exemplary non-metallic expandable braid, local MRI coil, and motion tracking coils that form a part of the catheter device of FIG. 1, in which the braid is in a deployed position.
Figure 3:
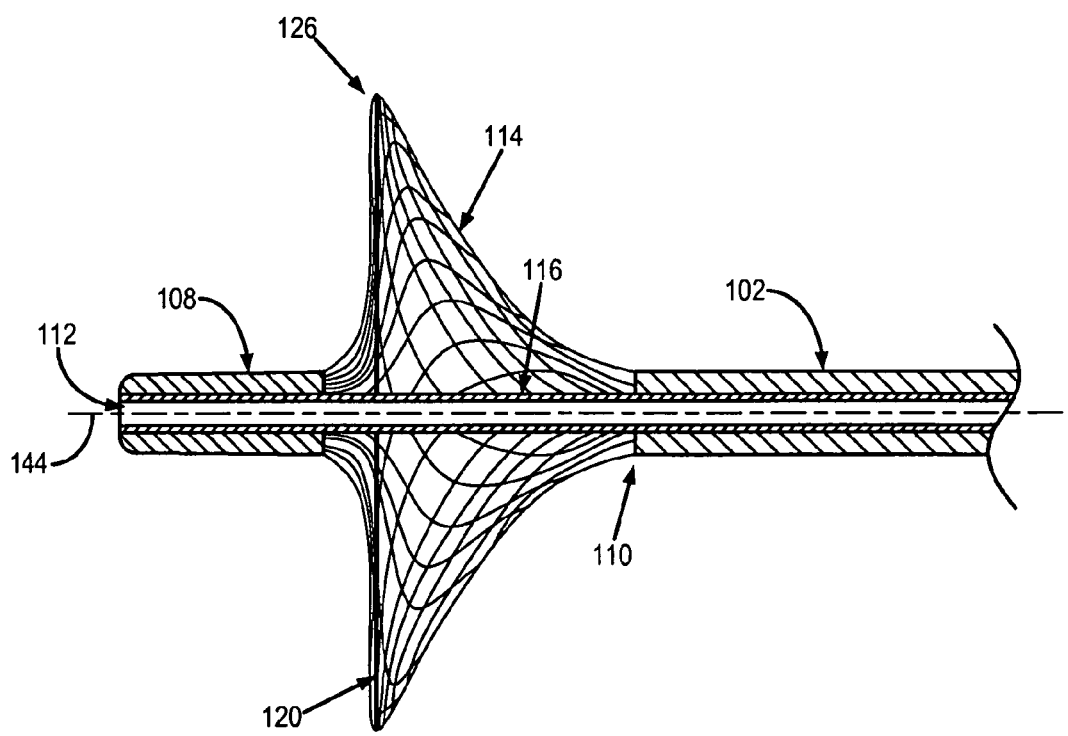
FIG. 3 is a cross-sectional view of the exemplary non-metallic expandable braid, local MRI coil, and motion tracking coils of FIG. 2.
Figure 4:
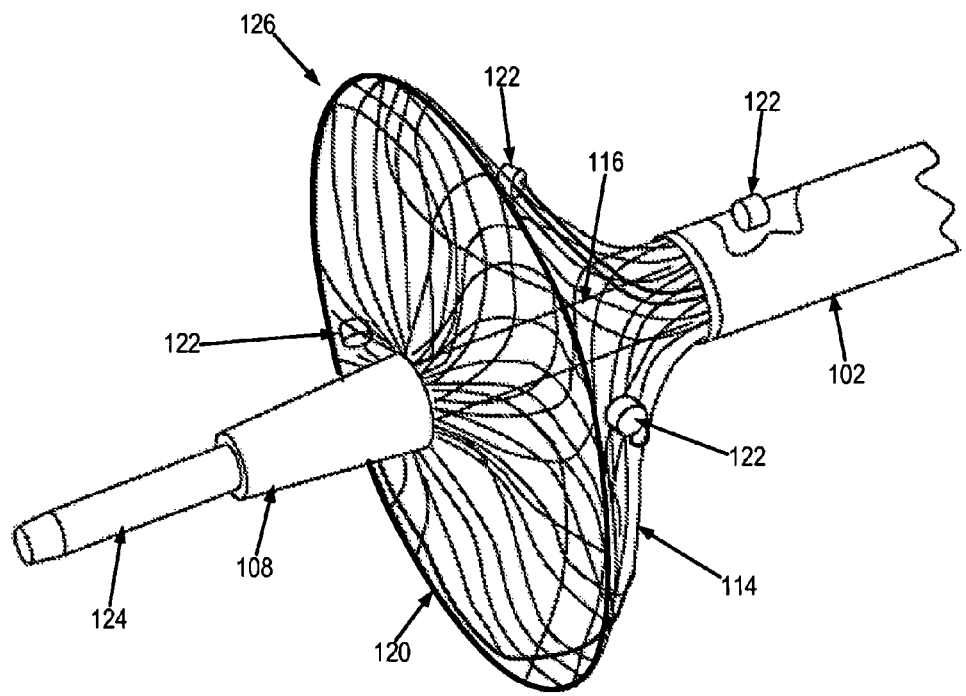
FIG. 4 is a perspective view of an exemplary non-metallic expandable braid, local MRI coil, and motion tracking coils that form a part of the catheter device of FIG. 1, and in which an exemplary radio frequency ablation ("RFA") catheter tip is shown as extending through the catheter device.
Figure 8:
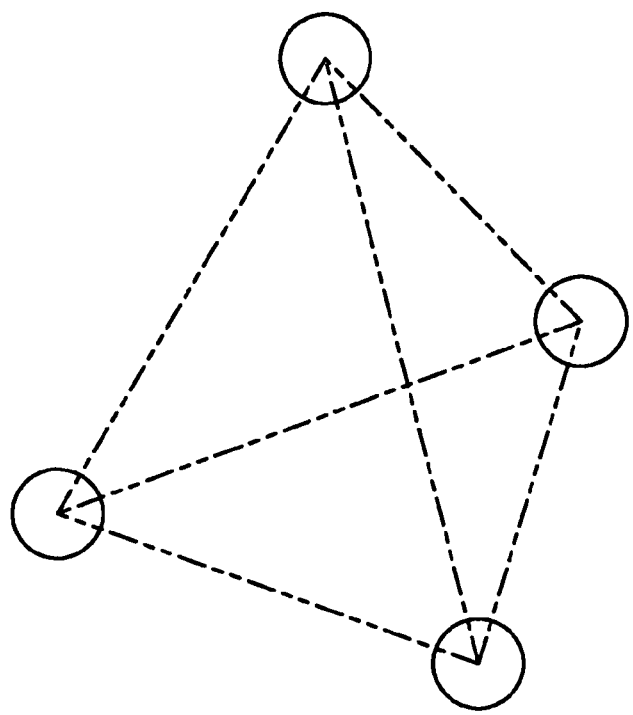
FIG. 8 is a pictorial representation of a tetrahedral arrangement of motion tracking coils.

Referring generally now to FIGS. 2 and 3, a magnetic resonance imaging coil 120 is coupled to the braid 114, for example, by being intertwined with the non-metallic filaments that form the braid 114. The magnetic resonance imaging coil 120 is shaped such that when the braid 114 is expanded to its deployed position, the magnetic resonance imaging coil 120 is substantially circular. In alternative configurations, the magnetic resonance imaging coil 120 may be elliptical or similar in shape. A plurality of motion tracking coils 122 may also coupled to the braid 114. Exemplary motion tracking coils 122 include solenoidal geometry micro-coils, but can also include other coil geometries. In some alternative configurations, the motion tracking coils 122 may be replaced with non-MRI positional tracking devices. An additional motion tracking coil 122 may also be positioned at and coupled to the distal end 110 of the outer catheter shaft 102 (FIG. 4). These motion tracking coils 122 may be positioned such that when the braid 114 is expanded to its deployed position, the motion tracking coils 122 are spaced in a polyhedral arrangement, such as a tetrahedron when four motion tracking coils 122 are provided, as illustrated in FIG. 8. While not necessary, this tetrahedral arrangement is preferable because it allows for the detection of motion occurring in all spatial directions, including both rotations and translations.

Referring again to FIG. 1, towards the proximal end 104 of the catheter device 100, the outer catheter shaft 102 and inner catheter shaft 116 are coupled to a fixture 140 that is in electrical communication with a radio frequency system coupling 142. The fixture 140 may be, for example, a Tuohy-Borst adapter. In some configurations, the fixture 140 may be configured to lock the relative positions of the inner catheter shaft 116 and the outer catheter shaft 102. Additionally, the fixture 140 may be configured to seal the inner catheter shaft 116 and the outer catheter shaft 102 to prevent unwanted blood flow through the catheter device 100.

The radio frequency system coupling 142 provides an electrical connection between the catheter device 100 and the radio frequency system of a magnetic resonance imaging system. For example, this connection provides a communication pathway for image data acquired with the magnetic resonance imaging coil 120 and motion tracking data acquired with the motion tracking coils 122. Central frequency tuning and impedance matching circuitry for the magnetic resonance imaging coil 120 may be positioned proximate the distal end 110 of the outer catheter shaft 102. For example, tuning and matching micro-circuitry may be coupled to the outer catheter shaft 102 so that the overall dimensions of the outer catheter shaft 102 are not undesirably increased.

The magnetic resonance imaging coil 120 is intertwined with the filaments that form the braid 114, and positioned such that it lies substantially in an edge portion 126 of the braid 114 when the braid 114 is in its deployed position. This positioning results in the magnetic resonance imaging coil 120 being substantially circular when the braid 114 is deployed, as illustrated, for example, in FIG. 7. Because the magnetic resonance imaging coil 120 is intertwined with the filaments that form the braid 114, when the braid 114 is retracted, the magnetic resonance imaging coil 120 is undulated over the braid 114, as illustrated, for example, in FIGS. 5 and 6. In alternative configurations, the magnetic resonance imaging coil 120 may be zigzagged within the walls of an elastomeric band that is coupled to the braid 114 or zigzagged within a sealed silicone micro-tubing that is coupled to the braid 114.

Referring now, generally, to FIGS. 2-7, the braid 114 is formed of a plurality of relatively thin continuous filaments having a cross section that is round, flat, or otherwise suitable to form a braid. The filaments forming the braid 114 are composed of a medical device class VI approved polymer material, such as, for example, polyethylene terephthalate ("PET"); however, other polymer materials could also be employed, such as other related PET formulations, polyethylene naphthalate ("PEN"), and polyether ether ketone ("PEEK"). Such materials have no measurable magnetic susceptibility, thereby providing a suitable substrate for the delivery and operation of a radio frequency coil for magnetic resonance imaging.

The filaments are generally arranged as follows. Each filament is paired with an opposing filament so that when the filaments are longitudinally compressed, the opposing filaments act upon each other to form the edge portion 126 of the braid 114. The filaments may be, for example, uniformly spaced around a perimeter of both the distal end 110 of the outer catheter shaft 102 and a perimeter of the inner catheter shaft 116, or a perimeter of the tip 108. Each filament extends from the distal end 110 of the outer catheter shaft 102 towards distal end of the inner catheter shaft 116, or the proximal end of the tip 108. As each filament extends from the distal end 110 of the outer catheter shaft 102 towards the distal end of the inner catheter shaft 116, or the proximal end of the tip 108, the filament is rotated through a pitch angle around a longitudinal axis 144 (FIG. 3) of the inner catheter shaft 116. The filaments are further arranged so that the spaces between filaments in the braid 114 are sized such that blood can freely flow through the braid 114. The braid 114 has a designated pitch, filament size, and filament volume, and inner diameter that all contribute to the overall profile of the braid 114.

Figure 5:
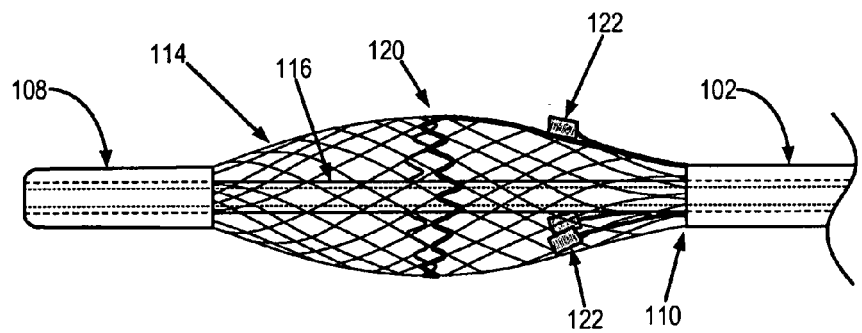
FIG. 5 is an elevation view of the exemplary non-metallic expandable braid, local MRI coil, and motion tracking coils of FIG. 2, in which the braid is in an intermediate position.
Figure 6:
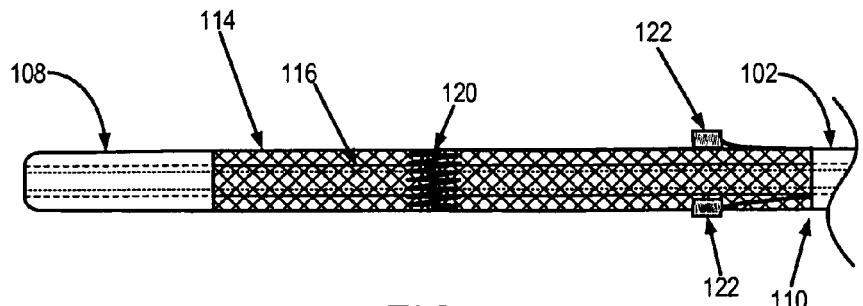
FIG. 6 is an elevation view of the exemplary non-metallic expandable braid, local MRI coil, and motion tracking coils of FIG. 2, in which the braid is in a retracted position.
Figure 7:
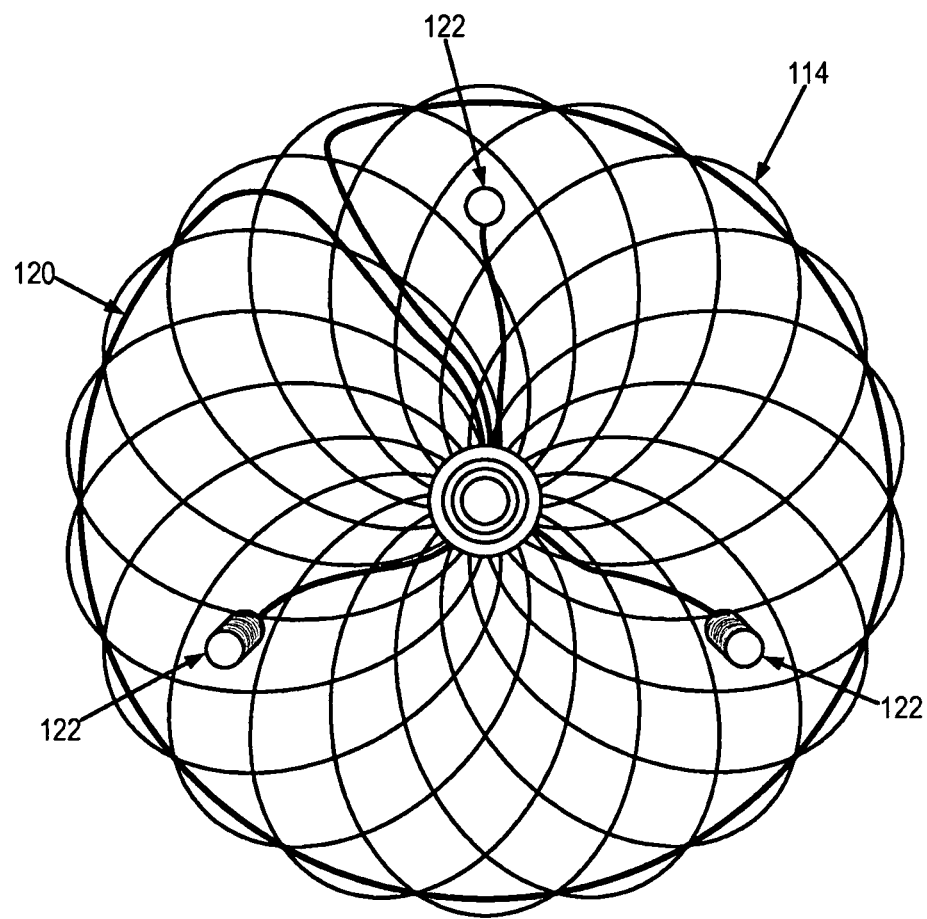
FIG. 7 is a plan view along the longitudinal axis of the exemplary non-metallic expandable braid in a deployed position, local MRI coil, and motion tracking coils of FIG. 2.

Referring particularly now to FIG. 6, in its retracted position, the braid 114 has a substantially cylindrical shape. As the distance between the distal ends of the outer catheter shaft 102 and inner catheter shaft 116 is shortened, the filaments in the braid 114 are longitudinally compressed and the braid 114 begins to expand, as illustrated in FIG. 5. As the distance between the distal ends of the outer catheter shaft 102 and inner catheter shaft 116 continues to shorten, the filaments in the braid 114 are further longitudinally compressed, until the braid 114 transitions to its deployed position, as illustrated in FIGS. 2-4. In this deployed position, the braid 114 transitions from the substantially-cylindrical, longitudinally continuous shape of the retracted position to create a cusp that forms an edge portion 126, about which the magnetic resonance imaging coil 120 is disposed. In particular, the cusp forming the edge portion 126 is created through the particular configuration of the collective filaments of the braid 114 in overlapping, and intertwining arrangement. This overlapping and intertwining arrangement is specifically designed such that the extension of a given, individual filament, when moving toward the deployed position, is restricted by those filaments overlapping and intertwined with the given filament to thereby cause the filament to take a form yielding a profile of opposing concave frustums. As referred to herein, the term "concave frustum" refers to a generally concave shape that is a surface of revolution of an exponential function. As referred to herein, the term "concave frustum" refers to a shape that is formed by cutting off the top of a cone by a plane parallel to the base of the cone, and in which the lateral surface of the cone curves inwards toward the axis of the cone.

Figure 9:
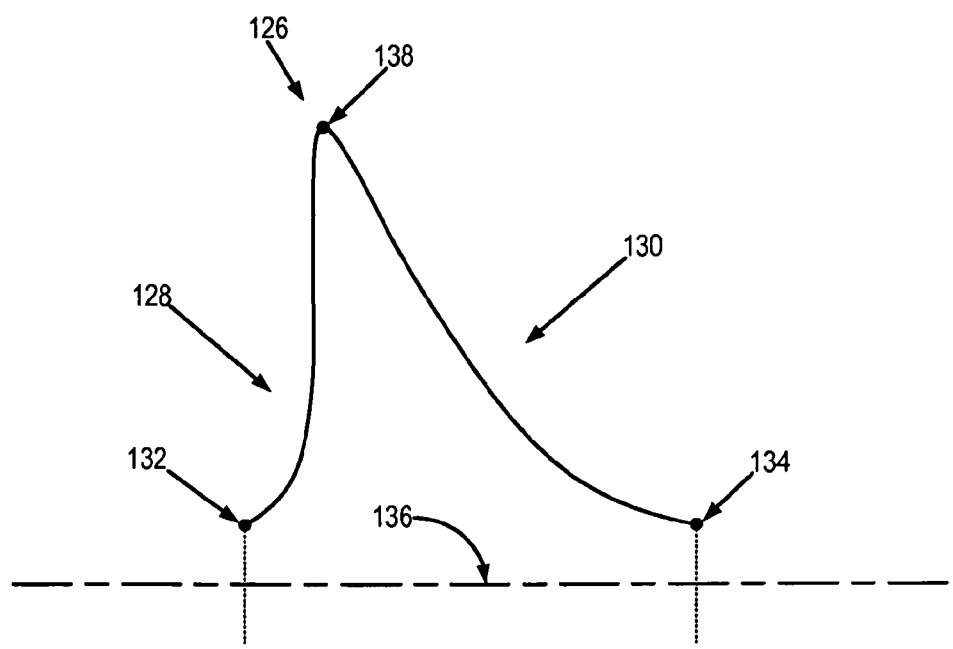
FIG. 9 is a graphic illustration of an exemplary profile of the expandable non-metallic braid of FIG. 2 in its deployed position.

Generally, the shape of the braid 114 in this deployed position is as follows. As stated, the braid 114 includes a cusp forming an edge portion 126 that is generally shaped as an annular region. Extending away from this edge portion 126 are two generally concave portions. These concave portions are shaped, for example, as concave frustums. An exemplary profile of the braid 114 in its deployed position is illustrated in FIG. 9, to which reference is now made. The profile is generally concave, having two distinct concave portions 128, 130 that meet at a common apex, which forms a cusp, in the edge portion 126. The profile of the braid 114 in the deployed position extends from a first point 132, such as a point on the inner catheter shaft 116 or tip 108, to a second point 134, such as a point on the distal end 110 of the outer catheter shaft 102. From the first point 132, the profile rises monotonically in a concave manner away from the an axis 136, such as the longitudinal axis 144 (FIG. 3) of the inner catheter shaft 116, to an apex 138 in the edge portion 126. From the apex 138, the profile then falls monotonically in a concave manner towards the second point 134.

Referring again to FIGS. 1-6, the mechanism that enables the braid 114 to transition between its retracted position and its deployed position is now described in more detail. The braid 114 is deployed by actuating the handle 118 of the catheter device 100 to slidably move the inner catheter shaft 116 longitudinally in the proximal direction. As the inner catheter shaft 116 moves longitudinally in the proximal direction, the distal end of the inner catheter shaft 116 is drawn closer to the distal end 110 of the outer catheter shaft 102. This result is the same in configurations where the inner catheter shaft 116 and the braid 114 are coupled to the tip 108 and the inner catheter shaft 116 is similarly actuated, or in some alternative configurations in which pull wires are provided in lieu of the inner catheter shaft 116 and these pull wires are similarly actuated. As a result of the distal end of the inner catheter shaft 116 being drawn nearer the distal end 110 of the outer catheter shaft 102, the distance between these two ends is shortened. This shortening of the distance between the distal end 110 of the outer catheter shaft 102 and the distal end of the inner catheter shaft 116 compresses the filaments that form the braid 114, thereby forcing the braid 114 to expand radially outward to its deployed position.

In an alternative configuration, the handle 118 may be coupled to the outer catheter shaft 102. In this configuration, actuation of the handle 118 slidably moves the outer catheter shaft 102 longitudinally in the distal direction. The result of this motion is, again, that the distance between the distal end 110 of the outer catheter shaft 102 and the distal end of the inner catheter shaft 116 is shortened. Thus, this motion similarly compresses the filaments that form the braid 114, thereby forcing the braid 114 to radially expand to its deployed position.

It should be appreciated that the braid 114 can be partially deployed by partial actuation of the handle 118, thereby actuating the braid 114 into an intermediate position, such as the one illustrated in FIG. 5. Even this intermediate position can be useful. For example, while the magnetic resonance imaging coil 120 may not be fully deployed in this intermediate position, the magnetic resonance imaging coil 120 can still be configured, for example, to be operated to acquire image data that can be used to image the general location of the braid 114.

Having generally described the features of the catheter device 100, a discussion of its general mode of operation is provided. By way of example, the operation of the catheter device 100 will be described with respect to a cardiac atrial fibrillation procedure in which an RFA device is provided to the catheter device 100 in order to provide ablation therapy to a patient. As noted above, it should be appreciated by those skilled in the art that the catheter device 100 can be employed for other procedures.

A target region of a left atrium is identified for treatment using an appropriate diagnostic procedure. Such procedures are well known in the art and are not described further herein. In the event that atrial ablation is desired, a physician makes a small incision in the body to gain access to a vascular pathway to the patient's heart. An initial guiding device, such as a guide wire, is used to guide the catheter device 100 to the target region. This guide wire is separate from the catheter device 100 and is used as a support for maneuvering the catheter device 100 through the pathway to the target region. When the guide wire is in position, the catheter device 100 is advanced so that the tip 108 of the catheter device 100 is positioned proximate to the target region.

The physician manipulates the handle 118 of the catheter device 100 in order to expand the braid 114 to its deployed position, after which the coil 120 is operated to acquire image data. When the brad 114 is in its deployed position, the fixture 140 can optionally be manipulated to lock and seal the catheter device 100 so that the braid 114 remains in the deployed position. From the acquired image data, images are reconstructed to confirm the location of the catheter device 100 in relation to the target region. In this way, the physician has a visual means of tracking the precise location of the catheter device 100. Motion information may also be acquired by the motion tracking coils 122 and this information utilized to correct the acquired image data for motion effects. Once the catheter device 100 is verified to be in the proper position using MRI, the guide wire is removed and an RFA device is advanced through the catheter device 100. The RFA device is operated to deliver radio frequency energy to the target region to heat the target region in accordance with a treatment plan. During the ablation treatment, image data may be acquired by the coil 120 and images reconstructed. For example, images that depict the temperature of the target region can be reconstructed so that an accurate and real-time assessment of the efficacy of the ablation treatment can be assessed. Motion information may also be acquired at this time by the motion tracking coils 122 and this information utilized to correct the acquired image data for motion effects.

Methods for acquiring and reconstructing magnetic resonance images are well known in the art, including those methods for acquiring magnetic resonance images that depict temperature changes in tissue. Additionally, methods for acquiring and utilizing motion tracking information with magnetic resonance imaging are well known in the art. For example, magnetic resonance signals can be acquired and their phase information used to assess motion of the subject from which the signals originated. Exemplary methods for motion tracking and motion compensation include so-called "navigator-echo" methods. Generally, motion compensation may include both prospective and retrospective motion compensation. In prospective compensation techniques, the acquired motion tracking information is used to correct the acquired image data for motion artifacts prior to or during image reconstruction. In retrospective compensation techniques, the motion tracking information is used to selectively sort images after they have been reconstructed, for example, by sorting the images according to cardiac or respiratory phase. An added value of the local motion tracking coils occurs in those situations in which various body tissues move at differing rates and when it is the goal of the targeted imaging to freeze the motion of the tissue-of-interest or region-of-interest alone. In such instances, the local motion tracking coils are more sensitive to motion of the tissue of interest due to their proximity and physical contact with it, so they provide a better estimate of this motion than is possible with surface-based MRI techniques.

Upon completion of the ablation treatment, the RFA device is removed from the catheter device 100 and optionally replaced with the guide wire. The physician then manipulates the handle 118 of the catheter device 100 to collapse the braid 114. The catheter device 100 is then removed from the patient's heart and backed out through the pathway. If the guide wire was used again, it is then removed from the patient in a similar fashion.

Figure 10:
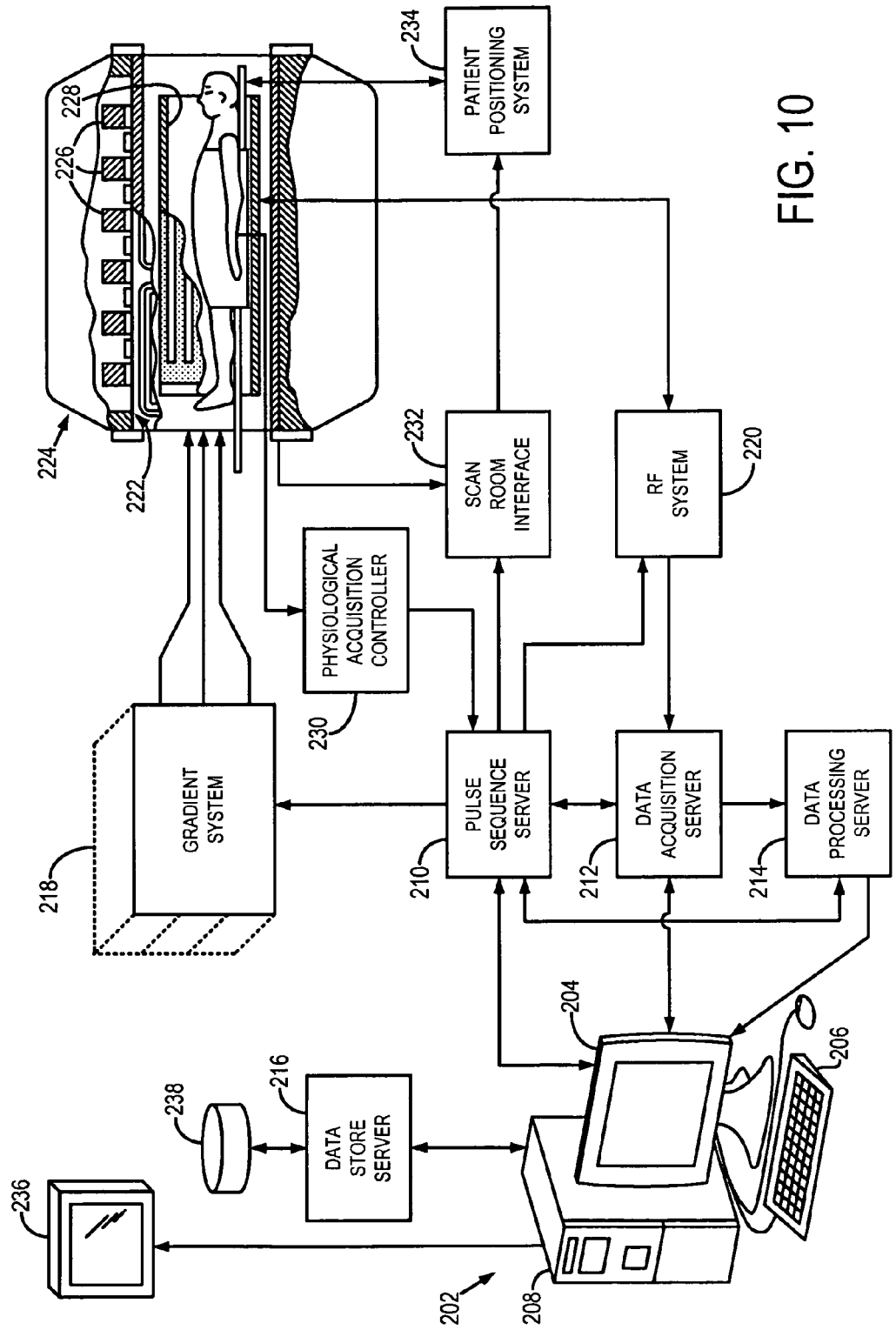
FIG. 10 is a block diagram of an exemplary MRI system configured for use with the catheter device of FIG. 1.

Referring particularly now to FIG. 10, an exemplary magnetic resonance imaging ("MRI") system 200 is illustrated. The MRI system 200 includes a workstation 202 having a display 204 and a keyboard 206. The workstation 202 includes a processor 208, such as a commercially available programmable machine running a commercially available operating system. The workstation 202 provides the operator interface that enables scan prescriptions to be entered into the MRI system 200. The workstation 202 is coupled to four servers: a pulse sequence server 210; a data acquisition server 212; a data processing server 214, and a data store server 216. The workstation 202 and each server 210, 212, 214 and 216 are connected to communicate with each other.

The pulse sequence server 210 functions in response to instructions downloaded from the workstation 202 to operate a gradient system 218 and a radiofrequency ("RF") system 220. Gradient waveforms necessary to perform the prescribed scan are produced and applied to the gradient system 218, which excites gradient coils in an assembly 222 to produce the magnetic field gradients $G_x$, $G_y$, and $G_z$ used for position encoding MR signals. The gradient coil assembly 222 forms part of a magnet assembly 224 that includes a polarizing magnet 226 and a whole-body RF coil 228.

RF excitation waveforms are applied to the RF coil 228, or a separate local coil (not shown in FIG. 10), by the RF system 220 to perform the prescribed magnetic resonance pulse sequence. Responsive MR signals detected by the RF coil 228, or a separate local coil (not shown in FIG. 10), are received by the RF system 220, amplified, demodulated, filtered, and digitized under direction of commands produced by the pulse sequence server 210. The RF system 220 includes an RF transmitter for producing a wide variety of RF pulses used in MR pulse sequences. The RF transmitter is responsive to the scan prescription and direction from the pulse sequence server 210 to produce RF pulses of the desired frequency, phase, and pulse amplitude waveform. The generated RF pulses may be applied to the whole body RF coil 228 or to one or more local coils or coil arrays (not shown in FIG. 10).

The RF system 220 also includes one or more RF receiver channels. Each RF receiver channel includes an RF amplifier that amplifies the MR signal received by the coil 228 to which it is connected, and a detector that detects and digitizes the I and Q quadrature components of the received MR signal. The magnitude of the received MR signal may thus be determined at any sampled point by the square root of the sum of the squares of the I and Q components:

$$M=\sqrt{I^2+Q^2} \tag{1};$$

and the phase of the received MR signal may also be determined:

$$\phi = \tan^{-1}\left(\frac{Q}{I}\right). \tag{2}$$

The pulse sequence server 210 also optionally receives patient data from a physiological acquisition controller 230. The controller 230 receives signals from a number of different sensors connected to the patient, such as electrocardiograph ("ECG") signals from electrodes, or respiratory signals from a bellows or other respiratory monitoring device. Such signals are typically used by the pulse sequence server 210 to synchronize, or "gate," the performance of the scan with the subject's heart beat or respiration.

The pulse sequence server 210 also connects to a scan room interface circuit 232 that receives signals from various sensors associated with the condition of the patient and the magnet system. It is also through the scan room interface circuit 232 that a patient positioning system 234 receives commands to move the patient to desired positions during the scan.

The digitized MR signal samples produced by the RF system 220 are received by the data acquisition server 212. The data acquisition server 212 operates in response to instructions downloaded from the workstation 202 to receive the real-time MR data and provide buffer storage, such that no data is lost by data overrun. In some scans, the data acquisition server 212 does little more than pass the acquired MR data to the data processor server 214. However, in scans that require information derived from acquired MR data to control the further performance of the scan, the data acquisition server 212 is programmed to produce such information and convey it to the pulse sequence server 210. For example, during prescans, MR data is acquired and used to calibrate the pulse sequence performed by the pulse sequence server 210. Also, navigator signals may be acquired during a scan and used to adjust the operating parameters of the RF system 220 or the gradient system 218, or to control the view order in which k-space is sampled. The data acquisition server 212 may also be employed to process MR signals used to detect the arrival of contrast agent in a magnetic resonance angiography ("MRA") scan. In all these examples, the data acquisition server 212 acquires MR data and processes it in real-time to produce information that is used to control the scan.

The data processing server 214 receives MR data from the data acquisition server 212 and processes it in accordance with instructions downloaded from the workstation 202. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 214 are conveyed back to the workstation 202 where they are stored. Real-time images are stored in a data base memory cache (not shown in FIG. 10), from which they may be output to operator display 212 or a display 236 that is located near the magnet assembly 224 for use by attending physicians. Batch mode images or selected real time images are stored in a host database on disc storage 238. When such images have been reconstructed and transferred to storage, the data processing server 214 notifies the data store server 216 on the workstation 202. The workstation 202 may be used by an operator to archive the images, produce films, or send the images via a network to other facilities.

The present invention has been described in terms of one or more preferred embodiments, and it should be appreciated that many equivalents, alternatives, variations, and modifications, aside from those expressly stated, are possible and within the scope of the invention.

The invention claimed is:

1. A catheter device for deploying a local magnetic resonance imaging coil, the catheter device comprising:
   an outer catheter shaft having a lumen extending from a proximal end to a distal end;
   an inner catheter shaft having a lumen extending along a longitudinal axis from a proximal end to a distal end, the inner catheter shaft being movably engaged with the outer catheter shaft;
   a plurality of non-metallic filaments, each non-metallic filament being attached on one end to the outer catheter shaft and coupled on another end to the inner catheter shaft, the plurality of non-metallic filaments being intertwined to form a braid;
   a local magnetic resonance imaging coil coupled to the braid and configured to have a substantially circular shape when the braid is in the deployed position;
   wherein shortening of a distance between the distal end of the outer catheter shaft and the distal end of the inner catheter shaft actuates the braid from a retracted position to the deployed position; and
   wherein the local magnetic resonance imaging coil is coupled to the braid such that when the braid is in the deployed position the local magnetic resonance imaging coil is in a plane perpendicular to the longitudinal axis of the inner catheter shaft.

2. The catheter device as recited in claim 1 in which the inner catheter shaft is configured to slidably move within the lumen of the outer catheter shaft.

3. The catheter device as recited in claim 2 further comprising a handle coupled to the inner catheter shaft and configured to slidably move the inner catheter shaft when actuated.

4. The catheter device as recited in claim 1 in which the inner catheter shaft is disposed within the lumen of the outer catheter shaft and the outer catheter shaft is configured to slidably move over the inner catheter shaft.

5. The catheter device as recited in claim 1 further comprising a tip distal to the distal end of the outer catheter shaft and coupled to the distal end of the inner catheter shaft.

6. The catheter device as recited in claim 5 in which the plurality of filaments are attached at one end to the distal end of the outer catheter shaft and coupled at another end to the tip.

7. The catheter device as recited in claim 1 further comprising a plurality of motion tracking coils coupled to the braid.

8. The catheter device as recited in claim 7 in which the motion tracking coils are substantially coplanar.

9. The catheter device as recited in claim 8 further comprising another motion tracking coil coupled to at least one of the outer catheter shaft and the inner catheter shaft.

10. The catheter device as recited in claim 9 in which the plurality of motion tracking coils and the another motion tracking coil are arranged to be spaced in a polyhedral arrangement when the braid is in the deployed position.

11. The catheter device as recited in claim 1 in which the non-metallic filaments are composed of a polymer.

12. The catheter device as recited in claim 11 in which the polymer includes at least one of polyethylene terephthalate, polyethylene naphthalate, and polyether ether ketone.

13. The catheter device as recited in claim 1 in which when the braid is in the deployed position the braid has a profile having an edge portion opposed by concave portions, and the local magnetic resonance imaging coil is positioned in the edge portion of the braid.

14. The catheter device as recited in claim 1 in which each of the plurality of non-metallic filaments rotates through a pitch angle as the non-metallic filament extends from the outer catheter shaft to the inner catheter shaft.

15. A local magnetic resonance imaging (MRI) coil system comprising:
    a catheter extending from a proximal end to a distal end to form a lumen extending therebetween;
    a shaft having a lumen extending along a longitudinal axis from a proximal end to a distal end, the catheter and shaft being movably engaged to move between a first position and a second position;
    a plurality of non-metallic filaments coupled to extend between the catheter and the shaft to form a braid configured to move between a retracted position and a deployed position as the catheter and shaft move between the first and second positions;
    a local MRI coil loop coupled to the braid and configured to compress with the braid in the retracted position and expand into a substantially circular shape with the braid in the deployed position; and
    wherein the local MRI coil loop is coupled to the braid such that when the braid is in the deployed position the local MRI loop coil is in a plane perpendicular to the longitudinal axis of the shaft.

16. The MRI coil system as recited in claim 15 in which the non-metallic filaments overlap in an intertwining arrangement to form the braid as a continuous cylinder when in the retracted position and an annular edge opposed on each side by a concave frustum when in the deployed position.

17. The MRI coil system as recited in claim 15 in which the shaft is positioned within the lumen of the catheter and configured to slidably move along a longitudinal axis of the catheter between the first position and the second position.

18. The MRI coil system as recited in claim 15 in which the shaft is positioned within the lumen of the catheter and the catheter is configured to slidably move along a longitudinal axis of the shaft between the first position and the second position.

19. The MRI coil system as recited in claim 15 further comprising a plurality of local motion tracking coils coupled to the braid and configured to compress with the braid in the retracted position and expand with the braid in the deployed position; and another local motion tracking coil coupled to at least one of the catheter and the shaft and configured to be spaced in a polyhedral arrangement with the plurality of local motion tracking coils when the braid is in the deployed position.

20. The MRI coil system as recited in claim 19 in which the plurality of local motion tracking coils includes three motion tracking coils and the polyhedral arrangement is a tetrahedral arrangement.

21. A catheter device for deploying a local magnetic resonance imaging coil, the catheter device comprising:
    an outer catheter shaft having a lumen extending longitudinally from a proximal end to a distal end;
    an inner catheter shaft having a lumen extending longitudinally along a longitudinal axis from a proximal end to a distal end, the inner catheter shaft and the outer catheter shaft being movably engaged;
    a plurality of non-metallic, intertwining filaments forming a braid and engaged with at least one of the outer catheter shaft and the inner catheter shaft to move between a retracted position and a deployed position in which the braid forms a cusp;
    a local magnetic resonance imaging coil coupled to the braid to extend about an apex of the cusp of the braid when the braid is in the deployed position; and
    wherein the local magnetic resonance imaging coil is coupled to the braid such that when the braid is in the deployed position the local magnetic resonance imaging coil is in a plane perpendicular to the longitudinal axis of the inner catheter shaft.

22. The catheter device of claim 21 in which the plurality of non-metallic, intertwining filaments forming the braid are arranged as a continuous cylinder when in the retracted position.

* * * * *

UNITED STATES PATENT AND TRADEMARK OFFICE
CERTIFICATE OF CORRECTION

PATENT NO. : 8,983,574 B2
APPLICATION NO. : 13/509719
DATED : March 17, 2015
INVENTOR(S) : Schmidt et al.

Page 1 of 1

It is certified that error appears in the above-identified patent and that said Letters Patent is hereby corrected as shown below:

In the claims

Column 10, Claim 1, line 40, "is in" should be --is oriented in--.

Column 11, Claim 15, line 38, "is in" should be --is oriented in--.

Column 12, Claim 21, line 40, "is in" should be --is oriented in--.

Signed and Sealed this
Eighteenth Day of August, 2015

Michelle K. Lee
*Director of the United States Patent and Trademark Office*